United States Patent [19]

Gray

[11] Patent Number: 4,823,594

[45] Date of Patent: Apr. 25, 1989

[54] CONTAINER FOR A FLUID TO BE TESTED UNDER PRESSURE

[75] Inventor: Dennis W. Gray, Comanche, Okla.

[73] Assignee: Halliburton Company, Duncan, Okla.

[21] Appl. No.: 167,830

[22] Filed: Mar. 14, 1988

[51] Int. Cl.$^4$ ............................................. G01N 11/10
[52] U.S. Cl. ............................................. 73/54; 73/59
[58] Field of Search .................. 73/59, 54; 92/93, 96, 92/98 R, 99, 100, 105

[56] References Cited

U.S. PATENT DOCUMENTS

| | | | |
|---|---|---|---|
| 2,096,222 | 10/1937 | Bock | 265/11 |
| 2,122,765 | 7/1938 | Weiler | 265/11 |
| 2,266,733 | 12/1941 | Bays et al. | 265/11 |
| 2,626,786 | 1/1953 | McGlothlin | 259/8 |
| 3,027,756 | 4/1962 | Head | 73/53 |
| 3,285,057 | 11/1966 | De Zurik | 73/59 |
| 3,402,729 | 9/1968 | Richmond et al. | 137/92 |
| 3,636,753 | 1/1972 | Thiele et al. | 73/59 |
| 3,751,975 | 8/1973 | Katsura | 73/59 |
| 4,175,425 | 11/1979 | Brookfield | 73/59 |
| 4,175,590 | 11/1979 | Grandclement | 92/98 R |
| 4,430,889 | 2/1984 | Sutton | 73/61.4 |
| 4,466,276 | 8/1984 | Royak et al. | 73/54 |
| 4,653,313 | 3/1987 | Sabins et al. | 73/61.4 |
| 4,668,911 | 5/1987 | Mueller et al. | 324/208 |

FOREIGN PATENT DOCUMENTS

| | | | |
|---|---|---|---|
| 1184119 | 12/1964 | Fed. Rep. of Germany | 73/59 |
| 2920084 | 11/1980 | Fed. Rep. of Germany. | |
| 568869 | 11/1977 | U.S.S.R. . | |
| 594438 | 2/1978 | U.S.S.R. . | |
| 650009 | 4/1979 | U.S.S.R. . | |
| 670855 | 6/1979 | U.S.S.R. . | |

Primary Examiner—Michael J. Tokar
Assistant Examiner—M. Simons
Attorney, Agent, or Firm—Mark E. McBurney; E. Gilbert Harrison, III

[57] ABSTRACT

A slurry container for use in a consistometer to test a cement slurry includes a cup and a sealed pressure communicating structure. The sealed pressure communicating structure includes a baffle plate, a thermocouple well threadedly connected to an internal surface of a neck portion of the baffle plate, and a diaphragm extending radially between an outer surface of the neck portion of the baffle plate and an inner surface of the cup and longitudinally between facing surfaces of the baffle plate and a flange of the thermocouple well. A paddle is mounted on a shaft which is pivoted between the lower end of the thermocouple well and the bottom of the cavity defined in the cup. Magnets are mounted on the paddle to provide magnetic coupling across the sealed boundary defined by the baffle plate, thermocouple well and diaphragm assembly.

16 Claims, 2 Drawing Sheets

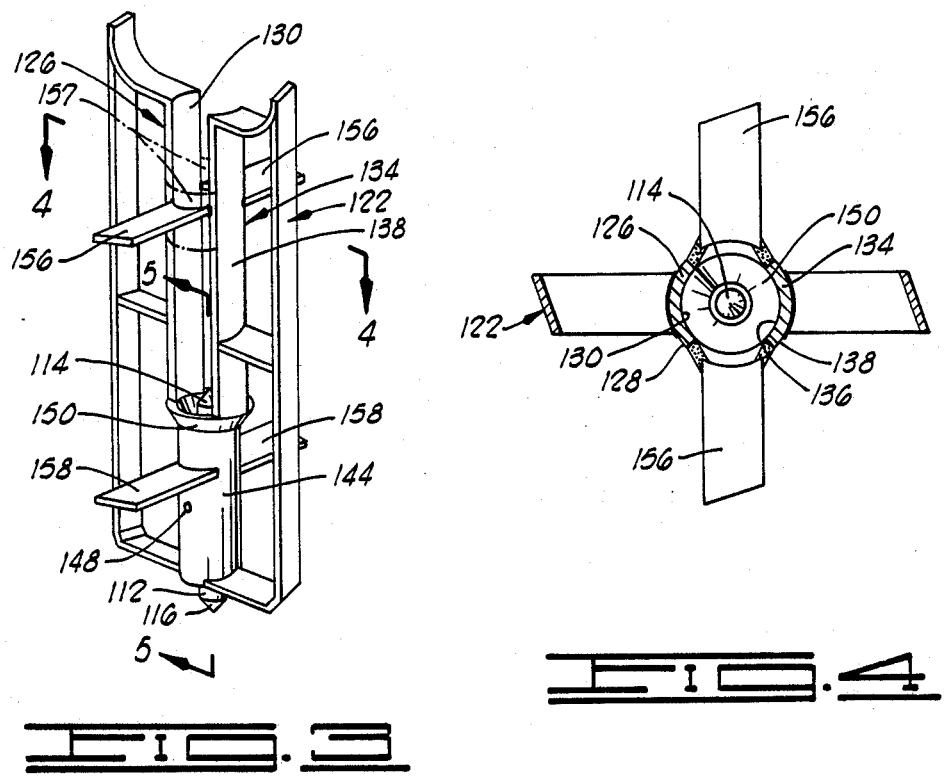
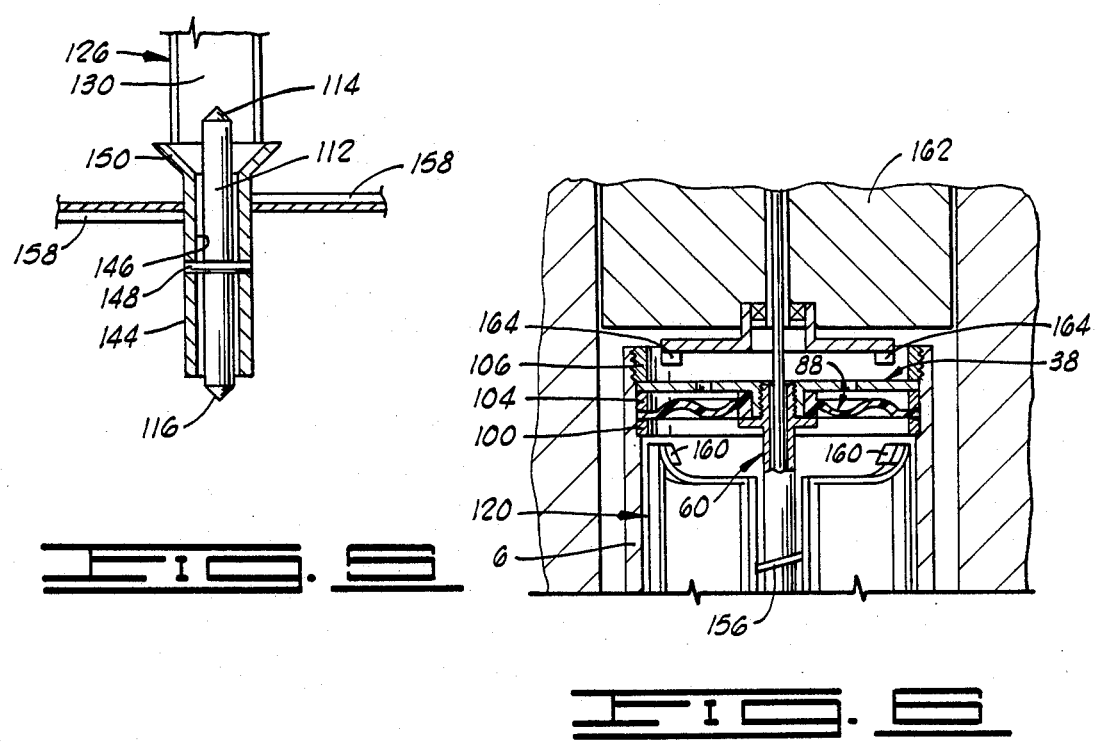

CONTAINER FOR A FLUID TO BE TESTED UNDER PRESSURE

BACKGROUND OF THE INVENTION

This invention relates generally to a container for a fluid to be tested under pressure and more particularly, but not by way of limitation, to a positive sealed slurry cup for a consistometer.

In the oil and gas industry, different fluids are used for various purposes in drilling and completing a well. For example, batches of cement slurry must be mixed and pumped into the well for cementing casing into the well bore. The cement is generally pumped through the casing and up the annulus between the casing and the well bore to create the necessary bond.

Because different batches of fluids (e.g., cement slurries) can have different characteristics which affect how the fluids perform in the high temperature and high pressure environments found downhole, there is the need for equipment which can test a fluid sample prior to the fluid being pumped downhole so that one can determine if that particular batch of fluid has the proper characteristics for the particular situation. Such a type of equipment, known as a consistometer or viscometer, is known to the art.

To pressurize the fluid under test in a consistometer of a type known to the art, a pressurized fluid is applied to one side of a sealed boundary separating the pressurized fluid from the test fluid. Not only must a seal be provided at this boundary, but also a sealed passageway through the seal must be provided to receive a paddle shaft or a tube in which a thermocouple is housed for monitoring the temperature of the test fluid. Heretofore, this passageway has been provided through one or more diaphragms or plates sealing directly around the shaft or tube. These diaphragms or plates extend across the annulus between the outside of the tube or shaft and the inside of the cup in which the test fluid is held. A diaphragm and bushing construction wherein O-rings carried by the bushing seal against the tube or shaft has also been used.

A shortcoming of these types of constructions is that when enough air bubbles are contained within the test fluid, the diaphragms or seal rings or plates of these prior constructions tend to collapse or deform toward the test fluid when the pressurized fluid is applied. This collapsing or deforming can break the seal formed at the edge where the seal member is to engage the tube or shaft extending therethrough, thus allowing the pressurized fluid to leak into the chamber where the test fluid is. The pressurized fluid, such as mineral oil, can contaminate the test fluid or can create a thin film on the inner surface of the cup containing the test fluid. This contamination or film can adversely affect the accuracy of the pumping time or viscosity analyses which were intended to be made.

Another noted shortcoming of these constructions which attempt to seal around a rotatable shaft is that excess friction may result when the shaft is rotated, such as in response to increasing viscosity of the test fluid, for example.

Therefore, there is the need for a new container for a fluid to be tested under pressure wherein the test fluid is more positively isolated from the pressure medium while still being able to rotate or detect the rotation of a paddle through the test fluid and while also still being able to receive a thermocouple for monitoring the temperature of the test fluid. Such a container should be specifically useful for high pressure, high temperature cement slurry testing consistometers.

SUMMARY OF THE INVENTION

The present invention overcomes the above-noted and other shortcomings of the prior art by providing a novel and improved container for a fluid to be tested under pressure. In the preferred embodiment, the present invention more positively isolates a cement slurry from a pressure medium and yet detects or imparts rotation of a paddle disposed in the cement slurry and monitors the temperature of the slurry.

The container of the present invention comprises: a cup having defined therein a cavity for receiving a fluid to be tested under pressure; a first member retained within the cup near a mouth of the cavity, the first member including a neck portion extending toward a closed end of the cavity, the neck portion having an outer surface; a second member retained within the cavity so that at least a part of the second member is disposed within the neck portion of the first member, the second member including a flange adjacent the neck portion and extending beyond the outer surface of the neck portion; and seal means for providing a seal from adjacent the neck portion of the first member and the flange of the second member to the cup so that the seal means is between the first member and the closed end of the cavity to separate a pressurizing medium, communicated through the first member to the seal means, from a fluid received in the cavity to be tested under the pressure exerted by the pressurizing medium.

In the preferred embodiment the neck portion of the first member has a cylindrical, threaded inner surface defining a throat through the neck portion. The first member also includes an annular disk portion which extends radially outwardly from an end of the neck portion. The second member further includes a tube portion including an open end and a closed end, which open end has a threaded outer surface engaged with the threaded inner surface of the neck portion of the first member and which open end has the flange of the second member extending therefrom adjacent the threaded outer surface. The closed end of the tube is disposed in the cavity of the cup. A diaphragm included in the seal means includes a hub disposed around the outer surface of the neck portion of the first member and between the annular disk portion of the first member and the flange of the second member.

The container further comprises a paddle and a shaft. The paddle includes a paddle frame, first center support means for supporting the paddle frame and for receiving a portion of the second member, and second center support means for supporting the first center support means and the paddle frame. The shaft is retained in the second center support means so that a first end of the shaft extends therefrom into pivotal engagement with the portion of the second member received into the first center support means and further so that a second end of the shaft extends therefrom into pivotal engagement with the cup at the closed end of the cavity. In the preferred embodiment, the container still further comprises at least one magnet mounted on the paddle frame.

Using one or more magnets on the paddle along with attracting magnet(s) mounted opposite the paddle magnet(s) on a viscosity measuring device or a paddle rotating system, whereby the boundary between the test slurry and the pressurizing fluid need not be invaded for measuring viscosity or for rotating, enables this slurry cup design to be used to give a positive seal between the test slurry and the pressurizing fluid. The mounting arrangement for the magnets may vary from that shown on the subsequently described drawings to achieve the desired magnetic attraction between the attracting magnet pairs.

Therefore, from the foregoing, it is a general object of the present invention to provide a novel and improved container for a fluid to be tested under pressure. Other and further objects, features and advantages of the present invention will be readily apparent to those skilled in the art when the following description of the preferred embodiment is read in conjunction with the accompanying drawings.

BRIEF DESCRIPTION OF THE DRAWINGS

FIG. 3 is a perspective view of a paddle and shaft subassembly of the container.

FIG. 4 is a sectional view of the paddle and shaft taken along line 4—4 shown in FIG. 3.

FIG. 5 is a partial sectional view of the paddle and shaft taken along line 5—5 shown in FIG. 3.

FIG. 6 is a partial sectional and schematic view of the container in a consistometer further including a potentiometer which is responsive to rotation of the paddle within the container.

DETAILED DESCRIPTION OF THE PREFERRED EMBODIMENT

Figure 1:
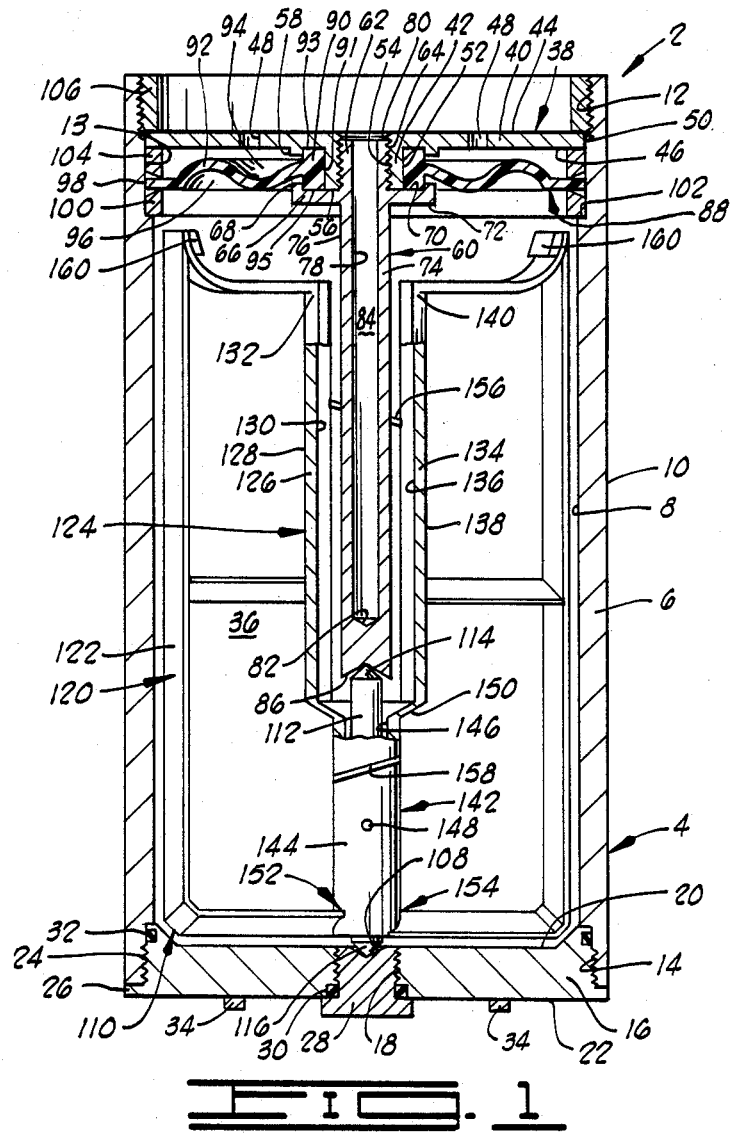
FIG. 1 is a sectional elevational view of a preferred embodiment of the container of the present invention.
Figure 2:
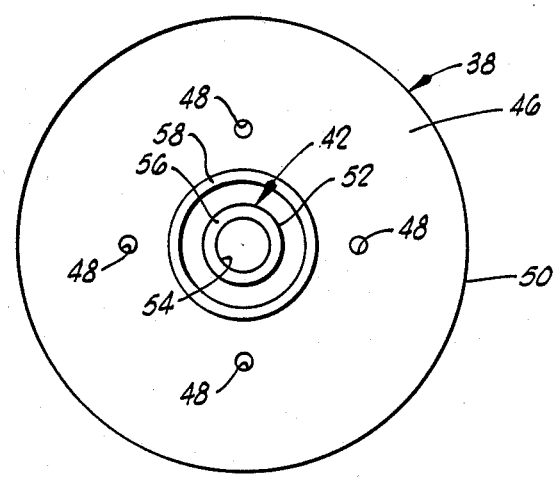
FIG. 2 is a bottom view of a baffle plate of the container.

The present invention provides a container for a fluid to be tested under pressure. In its preferred embodiment shown in the drawings, the container is a slurry container 2 suitable for testing cement slurries under high pressure and high temperature conditions while keeping the cement slurry under test isolated from the pressurizing medium. It is contemplated that other fluids can be tested in the container of the present invention.

The slurry container 2 includes a cup 4. The cup 4 includes a cylindrical sleeve 6 including a cylindrical inner surface 8 and a cylindrical outer surface 10. At the upper end of the sleeve 6 as it is shown in FIG. 1, the inner surface 8 has an indented threaded portion 12. Immediately below the threaded portion 12 is a smooth portion 13 to center subsequently identified baffle plate 38, diaphragm sealing ring 104, diaphragm 88 and diaphragm support ring 100. At the lower end of the sleeve 6 as shown in FIG. 1, the inner surface 8 has an indented threaded portion 14.

The cup also includes an annular base 16 having a central threaded opening 18 extending between side surfaces 20, 22 of the base 16. The circumferential edge of the base 16 has a threaded portion 24 and a flange portion 26.

The central opening 18 of the base 16 provides a drainage port from the cup 4. To block this port, a plug 28 is threaded into the opening 18. An O-ring 30 disposed in a groove defined in the base 16 around the opening 18 seals against the plug 28.

The base 16 is connected to the sleeve 6 by threading the outer edge section 24 of the base 16 into the threaded portion 14 of the sleeve 6 until the flange portion 26 abuts the lower end of the sleeve 6 as shown in FIG. 1. This connection is sealed by an O-ring 32 disposed in a groove formed around the base 16 as illustrated in FIG. 1.

The base 16 also has protuberances or lugs or pins 34 extending perpendicularly from the surface 22 as shown in FIG. 1. These protuberances 34 are used to engage a means for rotating the cup 6 in a manner known to the art in conducting consistometer or viscometer tests.

With the base 16 connected to the sleeve 6, the surfaces 8, 20 define a cavity 36 within the cup 4. The cavity 36 receives the fluid, such as a cement slurry, which is to be tested under controlled pressure and temperature conditions within the container 2 of the present invention. Cavity 36, and thus also the cup 4, is closed at the lower end by the base 16 and is open at its upper end for receiving the remaining structure of the present invention.

Part of this remaining structure of the container 2 includes a circular baffle plate member 38 retained within the cup 4 near the mouth of the cavity 36 defined at its open end at the top of the cup 4 for the disposition thereof shown in FIG. 1. The baffle plate 38 includes an annular disk portion 40 extending radially outwardly from an end of a neck portion 42. The annular disk portion 40 has side surfaces 44, 46 between which perforations or holes 48 perpendicularly extend for communicating a pressurizing fluid applied from outside surface 44 down through the annular disk portion 40 to below the surface 46. The surfaces 44, 46 terminate at a circumferential end surface 50 which defines the diameter of the annular disk portion 40. This diameter is substantially the same as the inner diameter of the threaded portion 12 of the inner surface 8 of the cup sleeve 6.

The neck portion 42 extends perpendicularly from, and coaxially with, the annular disk portion 40. This extension is from the side surface 46 towards the closed end of the cavity 36 defined by the cup base 16. The neck portion 42 has a cylindrical shape defined by a cylindrical outer surface 52 and a threaded cylindrical inner surface 54, which surface 54 defines an axial opening throughout the length of the neck portion 42. The surfaces 52, 54 terminate at their lower ends at an end surface 56 of the neck portion 42. The opening defined by the inner surface 54 through the neck portion 42 can be referred to as a throat through the neck portion 42. This throat extends through the center of the baffle plate 38.

The baffle plate 38 of the preferred embodiment further includes a circular boss 58 spaced radially outwardly from the neck portion 42. The boss 58 extends perpendicularly from the surface 46 parallel to the extension of the neck portion 42 from the surface 46.

Forming another part of the slurry container 2 of the preferred embodiment of the present invention, and connected to the baffle plate 38 in the preferred embodiment, is an elongated member 60 specifically defining a thermocouple well into which a thermocouple (not illustrated) can be received for monitoring the temperature of the slurry received within the cavity 36.

In the preferred embodiment the elongated member 60 includes a tube having an open upper end section 62 with a threaded outer cylindrical surface 64 which engages the threaded inner surface 54 of the neck portion 42 of the baffle plate 38. That is, this open upper end section 62 is screwed into the throat of the neck portion 42.

Extending radially outwardly from this open upper end section 62 just below the lower extent of the threaded outer surface 64 is a flange 66 of the elongated member 60. The flange 66 extends radially outwardly beyond the diameter of the neck portion 42 as defined by the outer surface 52 thereof. Upstanding from the outer periphery of the flange 66 is a boss or rim 68 which, when the elongated member 60 is connected to the baffle plate 38, is spaced radially from the outer surface 52 of the neck portion 42 of the baffle plate 38 substantially the same distance as is the boss 58 of the baffle plate 38. Thus, the bosses 58, 68, the outer surface 52 of the neck portion 42, and the facing portions of the surface 46 of the baffle plate 38 and a surface 70 of the flange 66 define an annular channel or receptacle. The remaining portion of the surface 70 of the flange 66 is adjacent the lower surface 56 of the neck portion 42 of the baffle plate 38 when the elongated member 60 is connected to the baffle plate 38 as shown in FIG. 1; when the baffle plate 38 and the elongated member 60 are tightened together, a portion of the surface 70 of the flange 66 abuts the surface 56 of the neck portion 42.

Extending downwardly from a lower surface 72 of the flange 66 is a main body portion 74 of the tube of the elongated member 60. The main body portion 74 has a cylindrical outer surface 76 and a cylindrical inner surface 78, which surface 78 extends upwardly through the flange and upper end portions of the elongated member 60. The upper end of the surface 78 terminates at an end surface 80 where the mouth of the thermocouple well defined by the elongated member 60 of the preferred embodiment is located. The lower end of this thermocouple well is closed by an inner surface 82. Thus, the surfaces 78, 82 define a well, or cavity, 84 within the elongated member 60.

The lower end of the main body portion 74 of the elongated member 60 terminates at a concave surface 86 defining an indentation in the lower end of the elongated member 60. The concave surface 86 or identation defines a pivot support surface which is spaced vertically above the closed end of the cavity 36 defined by the base 16 of the cup 4.

Both the baffle plate 38 and the elongated member 60 are made of a suitable metal of a type as known to the art; therefore, the threaded connection between the surfaces 54, 64 is simply a metal-to-metal connection which would be susceptible to leaking the pressurizing fluid, such as mineral oil, applied from above the surface 44 of the baffle plate 38. As previously mentioned, such leakage is not desirable because it can cause inaccurate test results. To seal this connection, a diaphragm 88 is used in the preferred embodiment. The diaphragm 88 is of a conventional type known to the art. Specifically, the diaphragm 88 has a generally circular configuration with a cylindrical inner sealing portion, or hub, 90 disposed around the neck portion 42 of the baffle plate 38 and between the facing surface portions of the surface 46 of the baffle plate 38 and the surface 70 of the flange 66. Specifically, the hub 90 is retained within the annular channel or receptacle defined between the bosses 58, 68 and the outer surface 52 of the neck portion 42 of the baffle plate 38. An inner surface 91 of the hub 90 abuts the outer surface 52; an end surface 93 of the hub 90 abuts the surface 46 of the baffle plate 38; an end surface 95 of the hub 90 abuts the surface 70 of the flange 66.

Extending radially outwardly from the hub 90 is a sealing disk portion 92 having a serpentine or undulating cross-sectional appearance as shown in FIG. 1. The disk portion 92 has an upper surface 94 and a lower surface 96, both of which terminate at their radially outward extents at a circumferential end surface 98 defining a diameter of the diaphragm 88 which is substantially the same as the inner diameter of the threaded surface section 12 of the inner surface 8 of the cup sleeve 6. This outer periphery of the diaphragm 88 provides a seal adjacent the inner surface of the cup sleeve 6 when the diaphragm 88 is suitably retained within the cup 4. When the diaphragm 88 is so retained, the pressurizing fluid is communicated through the perforations 48 in the baffle plate 38 and against the upper surface 94 of the diaphragm 88. This deforms the disk portion 92 of the diaphragm 88 as necessary to exert a pressure on the cement slurry (or other test fluid) located below the lower surface 96 of the diaphragm 88. This deformation occurs, however, without breaking the seals made at the inner and outer extremities of the diaphragm 88.

The retention of the inner sealing of the diaphragm 88 is aided by the bosses 58, 68 which engage the hub 90 of the diaphragm 88 to prevent or reduce extrusion of the hub 90 under compression exerted either by the pressurizing fluid or by tightening between the baffle plate 38 and the elongated member 60. It is to be noted, however, that although the bosses 58, 68 are of assistance in retaining the diaphragm 88, the bosses 58, 68 are not required. The ability to apply a compressing force to the hub 90 by screwing the baffle plate 38 and the elongated member 60 closer, as limited only upon the blocking abutment of the flange 66 against the neck portion 42, enables adjusting of the force applied to the hub 90 of the diaphragm 88.

The retention of the outer periphery of the diaphragm 88 is made in a conventional manner in the preferred embodiment. Specifically, a diaphragm support ring 100 is positioned within the mouth of the cavity 36 so that it rests on an annular shoulder 102 of the inner surface 8 of the cup sleeve 6 at the bottom of the threaded section 12 thereof. The outer periphery of the surface 96 of the diaphragm 88 rests on top of the support ring 100. The diaphragm 88 is secured in this mounting atop the support ring 100 by a diaphragm sealing ring 104. Rings 100, 104 can have outer threaded surfaces to threadedly engage with the threaded inner surface portion 12 of the cup sleeve 6; however, this is not necessary because in the preferred embodiment this outer diaphragm retaining assembly is retained by a main retaining ring 106 which is screwed down along the threaded surface portion 12 into engagement with the outer periphery of the surface 44 of the baffle plate 38 which is interposed between the ring 104 and the ring 106 as shown in FIG. 1. Thus, it is apparent that the rings 100, 104, 106 define means for retaining both the baffle plate 38 and the diaphragm 88 within the cup 4 near the open end of the cup. This also retains the elongated tubular member 60 which is connected to the baffle plate 38. This retains the elongated member 60 so that it extends from the baffle plate 38 toward the closed end of the cup 4, but keeping the pivot support surface 86 at the lower end of the elongated member 60 spaced from the closed end of the cup 4.

The diaphragm 88 and the retaining means define the preferred embodiment of a seal means for providing a seal from adjacent the neck portion 42 of the baffle plate 38 and the flange 66 of the elongated member 60 to the inner surface of the cup 4 so that the seal means is between the baffle plate 38 and the closed end of the cavity 36 to separate the pressurizing medium communicated through the baffle plate 38 from the fluid received in the cavity 36 to be tested under the pressure exerted by the pressurizing medium. This defines a sealed chamber between the surface 96 of the diaphragm 88 and the surface 20 of the cup base 16, within which chamber the pivot support surface 86 of the elongated member 60 is located. The pivot support surface 86 is specifically located vertically above the plug 28 when the plug 28 is retained in the base 16, which plug 28 has a similar pivot support surface identified in FIG. 1 by the reference numeral 108. This is defined by a concave surface or identation, but one upwardly facing as opposed to the downwardly facing surface 86. The significance of these facing, spaced pivot support surfaces 86, 108 will become apparent during the following description of a rotatable member 110 forming another part of the slurry container 2 of the preferred embodiment of the present invention.

The rotatable member 110 is disposed wholly within the cavity 36 below the diaphragm 88. The rotatable member 110 is pivoted between the lower, closed end of the elongated member 60 and the closed end of the cavity 36.

In the preferred embodiment the rotatable member 110 includes a relatively short cylindrical shaft or pivot 112 having an upper conical pivot end 114 and a lower conical pivot end 116. The shaft 112 extends between the lower end of the elongated member 60 and the upper end of the plug 28 so that the pivot end 114 can pivot on the pivot support surface 86 and the pivot end 116 can pivot on the pivot support surface 108. To prevent excess friction, however, preferably some clearance is provided between the pivot points 114, 116 and the pivot support surfaces 86, 108.

The shaft 112 provides the axis of pivotation for a paddle 120 forming another part of the rotatable member 110. The paddle 120 includes an outer paddle frame 122 which is the same as the corresponding frame of a conventional API paddle used for measuring viscosity. Although the paddle frame 122 is conventional, the central supporting structure by which the frame is mounted and connected to the shaft 112 is not and is a further distinction of the present invention whereby an otherwise conventional paddle is adapted to cooperate with the sealing and through structure previously described.

The central supporting structure of the paddle 120 includes a center support means 124 for supporting the paddle frame 122 and for receiving a portion of the elongated member 60 including the pivot support surface 86. The center support means 124 includes an elongated support member or plate 126 which is longitudinally straight but laterally curved so that it has a convex outer surface 128 and a concave inner surface 130. The support member 126 is connected at its upper end to the paddle frame 122 as shown at 132. The support member 126 extends downwardly therefrom parallel to the elongated member 60.

Disposed diametrically opposite the support member 126 is a support member or plate 134 forming another part of the center support means 124. The elongated support member or plate 134 is shaped the same as the member 126 so that the member 134 has a concave inner surface 136 and a convex outer surface 138. The member 134 extends parallel to the elongated member 60 from a connection at its upper end to the paddle frame 122 as designated at 140.

The inner surface 130 of the support member 126 and the inner surface 136 of the support member 134 are spaced from each other sufficiently to define an opening into which the majority of the main body 74 of the elongated member 60 is received when the container 2 is assembled as in FIG. 1. The surfaces 130, 136 are also suitable spaced so that they do not engage the outer surface 76 of the elongated member 60 to prevent any frictional engagement therebetween when the paddle 120 rotates relative to the elongated member 60.

The central supporting structure also includes a center support means 142 for supporting the center support means 124 and the paddle frame 122 and for receiving the shaft 112 so that the paddle 120 is mounted on the shaft. The center support means 142 of the preferred embodiment includes a cylindrical sleeve 144 through which the shaft 112 extends. To mount the cylindrical sleeve 144 on the shaft 112, the shaft is inserted through the central opening defined by a cylindrical inner surface 146 of the sleeve 144 until the end 114 of the shaft 112 protrudes from one end of the sleeve 144 and the end 116 of the shaft 112 extends through the other end of the sleeve 144. With the shaft 112 and the sleeve 144 suitably positioned relative to each other, a pin 148 is driven or otherwise inserted through an opening in the sleeve 144 and into an opening in the shaft 112 to secure the two relative to each other.

The diameter of the sleeve 144 is sufficiently small so that it is radially inwardly offset from the diameter of the center support means 124. This provides a closer supporting engagement between the sleeve 144 and the shaft 112. To connect this narrower sleeve 144 to the two support members 126, 134 of the center support means 124, the paddle 120 further includes a frustoconical adapter section 150 which converges from the lower ends of the support members 126, 134 to the upper end of the sleeve 144 as shown in FIG. 1. Thus, the lower ends of the center support members 126, 134 are connected to the upper end of the sleeve 144. The lower end of the sleeve 144 is connected to the paddle frame 122 at 152, 154 shown in FIG. 1.

Two paddle blades 156 of conventional design are connected, such as by welding, to the center support members 126, 134 such as is shown in FIG. 3. To reinforce this connection, if needed, a sleeve or curved plate can be used as indicated by the dot-dash lining referenced with the numeral 157 in FIG. 3. Two conventional paddle blades 158 are connected to the sleeve 144 as also shown in FIG. 3, for example.

As is apparent from the foregoing description of the rotatable member 110, it is rotatable within the cavity 36 with the rigidly coupled shaft 112 and paddle 120 being pivotable along the axis defined through the shaft 112 between the pivot support surfaces 86, 108. In the preferred embodiment, pivotation of the rotatable member 110 is brought about by a change in the viscosity of the fluid under test as the cup 4 is rotated by a suitable conventional rotating means (not shown) coupled to the cup 4 by means of the protuberances or lugs or pins 34 depending from the base 16. That is, as the cup 4 is rotated, and suitable pressure and heat applied to the fluid under test contained within the cavity 36, the viscosity of the test fluid increases until eventually the paddle 120 responds by pivoting through the connected shaft 112. As known to the art, this movement of the paddle 120 is what is indicative of the viscosity; therefore, this movement must be observed to obtain a test result. In the preferred embodiment, the observation of paddle movement is to be made through a magnetic coupling which includes magnets 160 mounted on top of the paddle frame 122 as illustrated in FIG. 1. Magnet locations can vary depending upon the desired attraction strength with, and location of, coupled external magnets. For example, one alternative location is to mount the magnets 160 more centrally of the paddle such as on an extension from the top of the center support means 124.

Referring to FIG. 6, there is shown a schematic representation of a potentiometer, or other sensing device, 162 to which magnets 164 are connected. The magnets 164 are of suitable polarities to be attracted to the polarities of the magnets 160. Thus, as the magnets 160 move, the magnets 164 also move, thereby rotating the exemplary potentiometer 162, which is connected within an electrical circuit that generates an electrical signal responsive to the change in the potentiometer 162 setting as it moves with movement of the magnetically coupled magnets 160, 164.

Although the preferred embodiment has been described with reference to the cup 4 being driven and the paddle 120 being responsive to the viscosity, the present invention can be constructed so that the paddle 120 is moved by an external source which is coupled thereto through external magnets. That is, with reference to the schematic illustration of FIG. 6, the potentiometer 162 would be replaced by a motor having a rotor to which magnets corresponding to the magnets 164 would be connected so that as the rotor is driven the magnets 160, magnetically coupled to the magnets on the rotor, would likewise be driven. In any event, it is also contemplated that a suitable centering device would be used to hold the slurry container 2 and the external device with which the magnets 160 would cooperate centered and in alignment with each other during a test.

Thus, the present invention provides a positively sealed slurry container to better prevent contaminating the test slurry with the pressurizing fluid and thus to better insure accurate test results. Accordingly, the present invention is well adapted to carry out the objects and attain the ends and advantages mentioned above as well as those inherent therein. While a preferred embodiment of the invention has been described for the purpose of this disclosure, changes in the construction and arrangement of parts can be made by those skilled in the art, which changes are encompassed within the spirit of this invention as defined by the appended claims.

What is claimed is:

1. A container for cement slurry to be tested under pressure, comprising:
   a cup having defined therein a cavity for receiving cement slurry to be tested under pressure;
   a first member retained within said cup near a mouth of said cavity, said first member including a neck portion disposed at substantially the center of said first member and extending toward a closed end of said cavity, said neck portion having an outer surface;
   a second member retained within said cavity so that at least a part of said second member is disposed within said neck portion of said first member, said second member including a flange adjacent said neck portion and extending beyond said outer surface of said neck portion; and
   seal means for providing a seal from adjacent said neck portion of said first member and said flange of said second member to said cup so that said seal means is between said first member and the closed end of said cavity to separate a pressurizing medium, communicated through said first member to said seal means, from cement slurry received in said cavity to be tested under the pressure exerted by the pressurizing medium.

2. A container as defined in claim 1, further comprising a rotatable member disposed in said cavity, said rotatable member including a pivot extending between said second member and the closed end of said cavity.

3. A container as defined in claim 1, further comprising:
   a paddle, including:
      a paddle frame;
      first center support means for supporting said paddle frame and for receiving a portion of said second member; and
      second center support means for supporting said first center support means and said paddle frame; and
   a shaft retained in said second center support means so that a first end of said shaft extends therefrom into pivotal engagement with the portion of said second member received into said first center support means and further so that a second end of said shaft extends therefrom into pivotal engagement with said cup at the closed end of said cavity.

4. A container as defined in claim 3, further comprising at least one magnet mounted on said paddle frame.

5. A container for a fluid to be tested under pressure, comprising:
   a cup having defined therein a cavity for receiving a fluid to be tested under pressure;
   a first member retained within said cup near a mouth of said cavity, said first member including a neck portion extending toward a closed end of said cavity, said neck portion having an outer surface; said neck portion of said first member having a cylindrical, threaded inner surface defining a throat through said neck portion;
   a second member retained within said cavity so that at least a part of said second member is disposed within said neck portion of said first member, said second member including a flange adjacent said neck portion and extending beyond said outer surface of said neck portion, said second member further includes a tube including an open end and a closed end, said open end having a threaded outer surface engaged with said threaded inner surface of said neck portion of said first member and said open end having said flange of said second member extending therefrom adjacent said threaded outer surface, and said closed end disposed in said cavity of said cup; and
   seal means for providing a seal from adjacent said neck portion of said first member and said flange of said second member to said cup so that said seal means is between said first member and the closed end of said cavity to separate a pressurizing medium, communicated through said first member to said seal means, from a fluid received in said cavity to be tested under the pressure exerted by the pressurizing medium.

6. A container as defined in claim 5, further comprising a rotatable member disposed in said cavity, said rotatable member including a shaft pivotally engaged at one end with said closed end of said tube of said second member and at the other end with said cup at the closed end of said cavity.

7. A container as defined in claim 5, wherein:
said first member further includes an annular disk portion extending radially outwardly from an end of said neck portion; and
said seal means includes a diaphragm including a hub disposed around said outer surface of said neck portion of said first member and between said annular disk portion of said first member and said flange of said second member.

8. A container for a fluid to be tested under pressure, comprising:
a cup having defined therein a cavity for receiving a fluid to be tested under pressure;
a baffle member having a cylindrical neck portion extending towards said cavity and including at least one hole therein for communicating a pressure therethrough;
an elongated member engaged with said neck portion and disposed within said cavity, said elongated member including a pivot support surface spaced from a closed end of said cavity;
seal means for providing a seal between said elongated member and said cup so that a sealed chamber is defined within said cavity, said chamber having said pivot support surface of said elongated member disposed therein;
a shaft pivotally mounted between said pivot support surface and said cup at said closed end of said cavity; and
a paddle disposed in said chamber, said paddle including:
a paddle frame;
first support means for supporting said paddle frame and for receiving a portion of said elongated member including said pivot support surface; and
second support means for supporting said first support means and said paddle frame and for receiving said shaft so that said paddle is connected to said shaft.

9. A container as defined in claim 8, wherein:
said second support means includes a sleeve through which said shaft extends; and
said first support means includes:
a first elongated plate having a first end connected to said sleeve and having a second end connected to said paddle frame; and
a second elongated plate having a first end connected to said sleeve and having a second end connected to said paddle frame.

10. A container as defined in claim 9, wherein said paddle further includes:
a first pair of paddle blades connected to said first and second elongated plates; and
a second pair of paddle blades connected to said sleeve.

11. A container as defined in claim 8, further comprising at least one magnet mounted on said paddle frame.

12. A container for a fluid to be tested under pressure, comprising:
a cup having an open end and a closed end;
a circular baffle plate including a cylindrical neck through which an opening extends at the center of said baffle plate, said baffle plate further including at least one hole defined therein for communicating a pressurizing fluid across said baffle plate;
a thermocouple well including:
a tubular member including a first end screwed into said opening of said neck of said baffle plate, said tubular member further including a second end having a concavity defined therein; and
a flange extending radially outwardly from said tubular member beyond said neck of said baffle plate, said flange disposed adjacent said neck;
a circular diaphragm including a cylindrical inner sealing portion disposed around said neck of said baffle plate and between said flange of said thermocouple well and said baffle plate, and said diaphragm further including an outer sealing portion disposed adjacent said cup;
means for retaining said baffle plate and said diaphragm within said cup near said open end of said cup so that said tubular member of said thermocouple well extends from said baffle plate towards said closed end of said cup with said second end of said tubular member spaced from said closed end of said cup;
a shaft pivotally mounted between said closed end of said cup and said concavity of said second end of said tubular member; and
a paddle, including:
a cylindrical sleeve retained on said shaft, said sleeve disposed between said closed end of said cup and said second end of said tubular member;
a first support member connected to said sleeve and extending parallel to said tubular member;
a second support member connected to said sleeve dismetrically opposite said first support member and extending parallel to said tubular member; and
a paddle frame connected to said sleeve and to said first and second support members.

13. A container as defined in claim 12, wherein said paddle further includes:
a first pair of paddle blades connected to said first and second support members; and
a second pair of paddle blades connected to said sleeve.

14. A container as defined in claim 12, further comprising two magnets mounted on said paddle frame.

15. A container as defined in claim 12, wherein:
said baffle plate further includes a circular boss spaced radially outwardly from said neck and engaging said inner sealing portion of said diaphragm; and
said thermocouple well further includes a circular boss extending from said flange and engaging said inner sealing portion of said diaphragm.

16. A container as defined in claim 12, wherein said paddle further includes a frusto-conical adapter converging from said first and second support members to said sleeve.

* * * * *

UNITED STATES PATENT AND TRADEMARK OFFICE
CERTIFICATE OF CORRECTION

PATENT NO. : 4,823,594
DATED : April 25, 1989
INVENTOR(S) : Dennis W. Gray

It is certified that error appears in the above-identified patent and that said Letters Patent is hereby corrected as shown below:

In column 3, line 55 insert therefore the number -4- after the word "cup"

In column 8, line 5 delete [suitable] and insert therefore --suitably--

In column 12, line 37 delete [dismetrically] and insert therefore --diametrically--

Signed and Sealed this

Twelfth Day of December, 1989

*Attest:*

JEFFREY M. SAMUELS

*Attesting Officer*     *Acting Commissioner of Patents and Trademarks*